(12) United States Patent
Liu et al.

(10) Patent No.: US 8,084,265 B2
(45) Date of Patent: *Dec. 27, 2011

(54) METHOD AND PD/V2 O5 DEVICE FOR H2 DETECTION

(75) Inventors: Ping Liu, San Diego, CA (US); C. Edwin Tracy, Golden, CO (US); J. Roland Pitts, Lakewood, CO (US); R. Davis Smith, II, Golden, CO (US); Se-Hee Lee, Lakewood, CO (US)

(73) Assignee: Alliance for Sustianable Energy, LLC, Golden, CO (US)

( * ) Notice: Subject to any disclaimer, the term of this patent is extended or adjusted under 35 U.S.C. 154(b) by 492 days.

This patent is subject to a terminal disclaimer.

(21) Appl. No.: 12/059,356

(22) Filed: Mar. 31, 2008

(65) Prior Publication Data

US 2009/0053822 A1    Feb. 26, 2009

Related U.S. Application Data

(62) Division of application No. 10/239,977, filed on Jan. 29, 2003, now Pat. No. 7,419,635.

(30) Foreign Application Priority Data

May 5, 2001 (WO) .................. PCT/US01/14411

(51) Int. Cl.
    *G01N 33/00*    (2006.01)
(52) U.S. Cl. ................. 436/144; 422/82.01; 422/500
(58) Field of Classification Search ............... 436/144; 422/68.01, 500
    See application file for complete search history.

(56) References Cited

U.S. PATENT DOCUMENTS

| 4,282,272 | A | 8/1981 | Matsuhiro |
| 4,365,870 | A | 12/1982 | Morita |
| 4,661,320 | A | 4/1987 | Ito |
| 4,706,493 | A | 11/1987 | Chang |
| 4,832,468 | A | 5/1989 | Ito |
| 4,889,414 | A | 12/1989 | Rauh |
| 5,105,303 | A | 4/1992 | Ilhage |

(Continued)

FOREIGN PATENT DOCUMENTS

EP    0730189    9/1996
(Continued)

OTHER PUBLICATIONS

Liu, "Stable PdN2O5 Optical H2 Sensor", Journal of Electrochemical Society, H76-H80 (2002).

(Continued)

*Primary Examiner* — Sam P Siefke
(74) *Attorney, Agent, or Firm* — Paul J. White; John C. Stolpa; W. LaNelle Owens

(57) ABSTRACT

Methods and Pd/V$_2$O$_5$ devices for hydrogen detection are disclosed. An exemplary method of preparing an improved sensor for chemochromic detection of hydrogen gas over a wide response range exhibits stability during repeated coloring/bleaching cycles upon exposure and removal of hydrogen gas. The method may include providing a substrate. The method may also include depositing a V$_2$O$_5$ layer that functions as a H$_2$ insertion host in a Pd/V$_2$O$_5$ hydrogen sensor to be formed on said substrate. The method may also include depositing a Pd layer onto said V$_2$O$_5$ layer; said Pd layer functioning as an optical modulator.

4 Claims, 2 Drawing Sheets

U.S. PATENT DOCUMENTS

| | | | |
|---|---|---|---|
| 5,252,142 | A | 10/1993 | Matsuyama |
| RE34,469 | E | 12/1993 | Cogan |
| 5,708,735 | A | 1/1998 | Benson |
| 5,724,187 | A | 3/1998 | Varaprasad |
| 5,777,780 | A | 7/1998 | Terada |
| 5,831,760 | A | 11/1998 | Hashimoto |
| 5,864,994 | A * | 2/1999 | Graf et al. ............... 52/171.3 |
| 6,020,987 | A | 2/2000 | Baumann |
| 6,080,998 | A | 6/2000 | Shima |
| 6,111,684 | A | 8/2000 | Forgette |
| 6,277,589 | B1 | 8/2001 | Seibert |
| 6,293,847 | B1 | 9/2001 | Easter |
| 6,448,068 | B2 | 9/2002 | Seibert |
| 6,723,566 | B2 | 4/2004 | Lee |
| 6,859,297 | B2 | 2/2005 | Lee |
| 7,910,373 | B2 | 3/2011 | Liu |
| 2003/0227664 | A1 | 12/2003 | Agrawal et al. |
| 2004/0023595 | A1 | 2/2004 | Ping et al. |

FOREIGN PATENT DOCUMENTS

| | | |
|---|---|---|
| JP | 59180526 | 10/1984 |
| JP | 62257046 | 9/1987 |
| JP | 62257047 | 9/1987 |
| WO | 9606203 | 2/1996 |

OTHER PUBLICATIONS

Lee, "Microstructure Study of Amorphous Vanadium Oxide Thin Films Using Raman Spectroscopy", Journal of Applied Physics, vol. 92, No. 4, Aug. 15, 2002.

Liu, "Electrochromic and Chemothromic Performance of Mesoporous Thin-Film Vanadium Oxide", Solid State Ionics, 165, pp. 223-228 (2003).

International Search Report, dated Dec. 19, 2001, for International Application No. PCT/US2001/14411.

International Preliminary Examination Report, dated Sep. 17, 2002, for International Application No. PCT/US2001/14411.

Written Opinion, dated Jul. 24, 2002, for International Application No. PCT/US2001/14411.

Pyun, "Hydrogen Transport Through r.f. Magnetron Sputtered Amorphous and Crystalline WO3 Films", Journal of Alloys and Compounds, 244, 1996, 16-22.

Judeinstein, "Role of the Water Content on the Electrochromic Properties of WO3nH2O Thin Films", Materials Science & Engineering, 1989, 120-132.

Ito, "Hydrogen Detection Based on Coloration of Anodic Tungsten Oxide Film", Appl. Phys. Lett. vol. 60, Feb. 1992, 938-940.

Kim, "A Study on the Hydrogen Intercalation into rf-magnetron Sputtered Amorphous WO3 Film Using Cyclic Voltammetry Combined with Electrochemical Quartz Crystal Microbalance Technique", Solid State Ionics, North Holland Pub. Co. vol. 109, No. 1-2, Jun. 1, 1998, 81-87.

Faughnan et al., "Electrochromic Displays Based on WO3", Display Devices, 1980, Chapter 5, pp. 181-211, Edited by PANKOVE, Springer-Verlag.

Judeinstein, "Role of the Water Content on the Electrochromic Properties of WO3 n H2O Thin Films", Materials Science & Engineering, 1989, 129-132.

International Search Report, dated Jan. 21, 2002, for International Application No. PCT/US2001/14375.

Written Opinion, dated Oct. 16, 2002, for International Application No. PCT/US2001/14375.

USPTO Office Communication, dated Jun. 28, 2004, for U.S. Appl. No. 10/240,082.

USPTO Office Communication, dated Nov. 30, 2004, for U.S. Appl. No. 10/240,082.

USPTO Office Communication, dated Jul. 12, 2007, for U.S. Appl. No. 10/240,082.

USPTO Office Communication, dated Dec. 13, 2007, for U.S. Appl. No. 10/240,082.

USPTO Office Communication, dated Jun. 12, 2008, for U.S. Appl. No. 10/240,082.

USPTO Office Communication, dated Feb. 4, 2009, for U.S. Appl. No. 10/240,082.

USPTO Office Communication, dated Mar. 17, 2006, for U.S. Appl. No. 10/239,977.

USPTO Office Communication, dated Jul. 18, 2006, for U.S. Appl. No. 10/239,977.

Definition of "response time"; http://www.pc-education.mcmaster.ca/Instrumentation/terminology.

Definition of "lag time" and "rise time"; http://www.nwglde.org/glossary.html.

International Search Report, dated Jan. 10, 2001, for International Application No. PCT/US2001/24699.

International Preliminary Examination Report, dated Jun. 5, 2003, for International Application No. PCT/US2001/24699.

Lee et al. "Characterization of Ni-W Oxide Thin Film Electrodes", Solid State Ionics, 1998, vol. 109, pp. 303-310.

Lee et al, "Electrochromic Behavior of Ni-W Oxide Electrodes", Solar Energy Materials and Solar Cells, 1995, vol. 39, pp. 155-166.

Lampert, "Electrochromic Materials and Devices for Energy Efficient Windows", Solar Energy Materials, 1984, vol. 11, pp. 1-27.

Beni, "Ion-Insertion Electochomic Displays", Advances in Image Pickup and Display,1982, vol. 5, pp. 83-136.

Decker et al., "The Electrochromic Process in Non-Stoichiometric Nickel Oxide Thin Film Electrodes", Electrochima Acta, 1992, vol. 37, No. 6, pp. 1033-1038.

* cited by examiner

METHOD AND PD/V2 O5 DEVICE FOR H2 DETECTION

CROSS-REFERENCE TO RELATED PATENT APPLICATION

This application claims priority as a divisional of U.S. patent application Ser. No. 10/239,977, filed on Jan. 29, 2003 now U.S. Pat. No. 7,419,635 and entitled "Pd/$V_2O_5$ DEVICE FOR $H_2$ DETECTION" by Ping Liu, hereby incorporated by reference as if fully set forth herein.

CONTRACTUAL AGREEMENT

The United States Government has rights in this invention under Contract No. DE-AC3699GO10337 between the United States Department of Energy and the National Renewable Energy Laboratory, a division of the Midwest Research Institute.

BACKGROUND

The preferred embodiment relates to an ultra-stable vanadium oxide thin film structure for the detection of hydrogen gas. The hydrogen gas is dissociated on the Pd catalyst into H atoms, and the $V_2O_5$ layer on which the Pd is coated functions as a $H^+$ insertion host. The Pd layer is thus stabilized, which upon combination with hydrogen is chemochromically changed.

Hydrogen is a plentiful, clean, non-polluting fuel. Hydrogen is currently used in many industries, and the US demand for hydrogen is approximately 140 billion cubic feet per year and growing. However, hydrogen is explosive at 4% in air. Therefore, it is critical to measure, monitor, and control hydrogen wherever it is used.

In the gas detection art where sensors and measurement instrumentation for hydrogen gases detect and/or measure hydrogen, typically there is required a portable sensing device, a kit (where hydrogen gas detection and/or measurement is required in existing equipment), and sensor heads installed at points where hydrogen leaks are possible, or where monitoring is necessary (i.e. in internal combustion engines which operate using hydrogen as a fuel).

The problems associated with current $H_2$ detection devices is that these devices do not exhibit stable cycling during repeated coloring/bleaching processes and are encumbered by a narrow response range for detecting $H_2$.

DESCRIPTION OF RELATED ART

At present, $H_2$ detection may be accomplished through the use of various and sundry devices, including thin film Pd oxide devices. However, several problems or drawbacks are associated with the use of these hydrogen detecting devices. These problems are: they do not exhibit stable cycling during repeated coloring/bleaching processes; and, they are encumbered by a narrow response range for detecting hydrogen.

Inadequate cycling stability during coloring/bleaching processes and the narrow response range for detection of hydrogen gas, in the case of the Pd thin film is due to the fact that, in the presence of high concentrations of $H_2$, palladium hydride is formed and the sensor is destroyed.

SUMMARY

One aspect of the preferred embodiment is to provide an ultra-stable palladium vanadium oxide film structure and method for chemochromic detection of hydrogen.

Another aspect of the preferred exemplary method is to provide an ultra-stable palladium vanadium oxide structure for chemochromic detection of hydrogen that exhibits stable cycling during repeated coloring/bleaching processes.

A further aspect of the preferred exemplary method is to provide an ultra-stable vanadium oxide film structure for chemochromic detection of hydrogen in which the proton insertion material contributes to stabilize the palladium layer, and exhibits a wider response range for detecting $H_2$.

In general, the preferred exemplary method is accomplished by providing a palladium/vanadium oxide layer sensor device in which, a $V_2O_5$ thin film is coated on a transparent or glass substrate. Thereafter, a palladium layer is evaporated onto the $V_2O_5$ thin film. The palladium layer serves as a catalyst material that facilitates reaction with hydrogen gas. That is, the hydrogen gas is dissociated on the Pd catalyst into H atoms, which diffuse into the $V_2O_5$ film.

The vanadium oxide layer acts as a hydrogen insertion host while the palladium layer is responsible for optical modulation. The presence of an ion storage host is vital to the stability of the palladium layer, and the sensor formed therefrom exhibits a wide response range for detecting hydrogen and shows very stable cycling during repeated coloring/bleaching processes.

BRIEF DESCRIPTION OF THE DRAWINGS

FIG. 3 is a graph showing percent transmission versus cycle number as a measure of cycling stability for a 20 nm $VO_x$/30 nmPd sensor in an environment of 4% $H_2$.

DESCRIPTION

Due to the fact that Pd/$WO_3$ sensors are saturated in the presence of just 2% $H_2$, and the fact that Pd sensors in the presence of $H_2$ form palladium hydride that results in destruction of the sensor, there is a need in the interest of safety to provide a $H_2$ sensor that still signals a chemochromic response to $H_2$ over a wide response range and in excess of 2%.

A further need exists in the art of chemochromic detection of hydrogen for a sensor that exhibits stable chemochromic cycling during repeated coloring/bleaching processes upon exposure and removal of $H_2$.

The Pd/$V_2O_5$ hydrogen sensor is capable of providing a response above the narrow range of 2% hydrogen because, unlike $WO_3$, the $V_2O_5$ is not saturated as 2% $H_2$ or higher.

While not wishing to be bound by any theory as to why the Pd/$V_2O_5$ sensor is capable of functioning beyond the $H_2$ saturation point compared to a Pd/$WO_3$ sensor, it is nevertheless believed that, the Pd/$V_2O_5$ sensor structure does not change the thermodynamics of the system, i.e., if fully equilibrated, the Pd still forms a hydride; however, when a kinetically steady state is achieved, the sensor still has the capacity to detect high concentrations of hydrogen even in a higher than normal atmospheric pressurized hydrogen atmosphere.

Figure 1A:
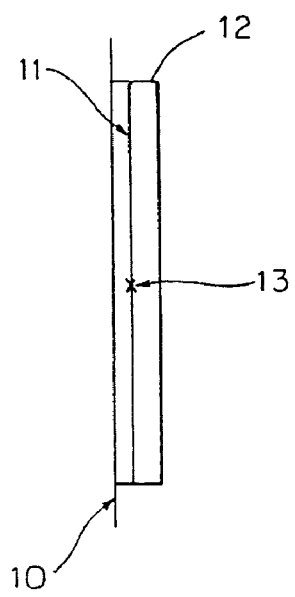
FIG. 1A shows a hydrogen sensor comprising $SiO_2$ deposited on a glass substrate, with Pd in turn deposited on the $SiO_2$ layer in which the interface between the $SiO_2$/Pd layer blocks the $H_2$.

Reference is now made to FIG. 1A in which there is shown a sensor comprising a glass substrate 10 on which is coated $SiO_2$, 11. A Pd layer 12 is coated onto the $SiO_2$. In this sensor device, as is depicted by arrow 13 directed onto the interface designated by x between the $SiO_2$ and Pd layers, $H_2$ 13 is blocked at the interface, because $SiO_2$ cannot react with hydrogen. Pd hydride is formed that undergoes phase transition at hydrogen concentration higher than 4%, resulting in substantial volume change and failure of the sensor.

Figure 1B:
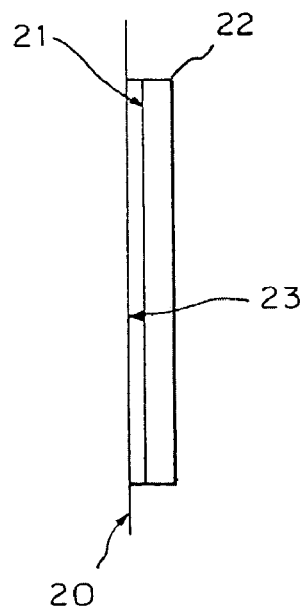
FIG. 1B shows a hydrogen sensor in which $V_2O_5$ is deposited on a glass substrate, with Pd in turn coated on the $V_2O_5$ layer in which the Pd/$V_2O_5$ interface does not block $H_2$.

On the other hand and by contrast, in FIG. 1B in which a glass substrate 20 is coated with a $V_2O_5$ layer 21, which in turn is coated by a Pd layer 22, $H_2$ 23 is not blocked at the interface between $V_2O_5$ and Pd. Accordingly, the vanadium oxide layer acts as a hydrogen insertion host in the Pd/$V_2O_5$ hydrogen sensor, while the palladium layer is responsible for the optical modulation.

The presence of an ion storage host is vital is vital to the stability of the palladium layer, and, unlike the case, when $SiO_2$ is used in conjunction with a Pd layer, the Pd layer does not peel off and is not degraded in the presence of 2% $H_2$ (but actually starts forming hydride at room temperature in the presence of about 4% $H_2$).

The insertion of hydrogen in the $V_2O_5$ is governed by the following equation:

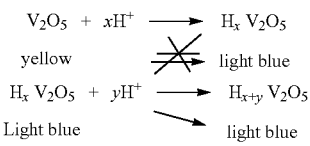

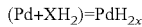

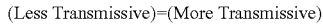

A control experiment was performed to show that the optical response was from the palladium layer.

The optical modulation is governed by the following equation:

(Pd+$XH_2$)=Pd$H_{2x}$ (Less Transmissive)=(More Transmissive)

A hydrogen sensor of Pd/$V_2O_5$ was then prepared in which the $V_2O_5$=2014 Å and the Pd=31 Å.

A cathodic optical response of 2% transmittance change is observed, and this compels the conclusion that the Pd layer is contributing to the optical response of the sensor, but that the $V_2O_5$ layer acts as a non-coloring ion storage layer and operates to stabilize the entire chemochromic hydrogen detector structure.

Figure 2:
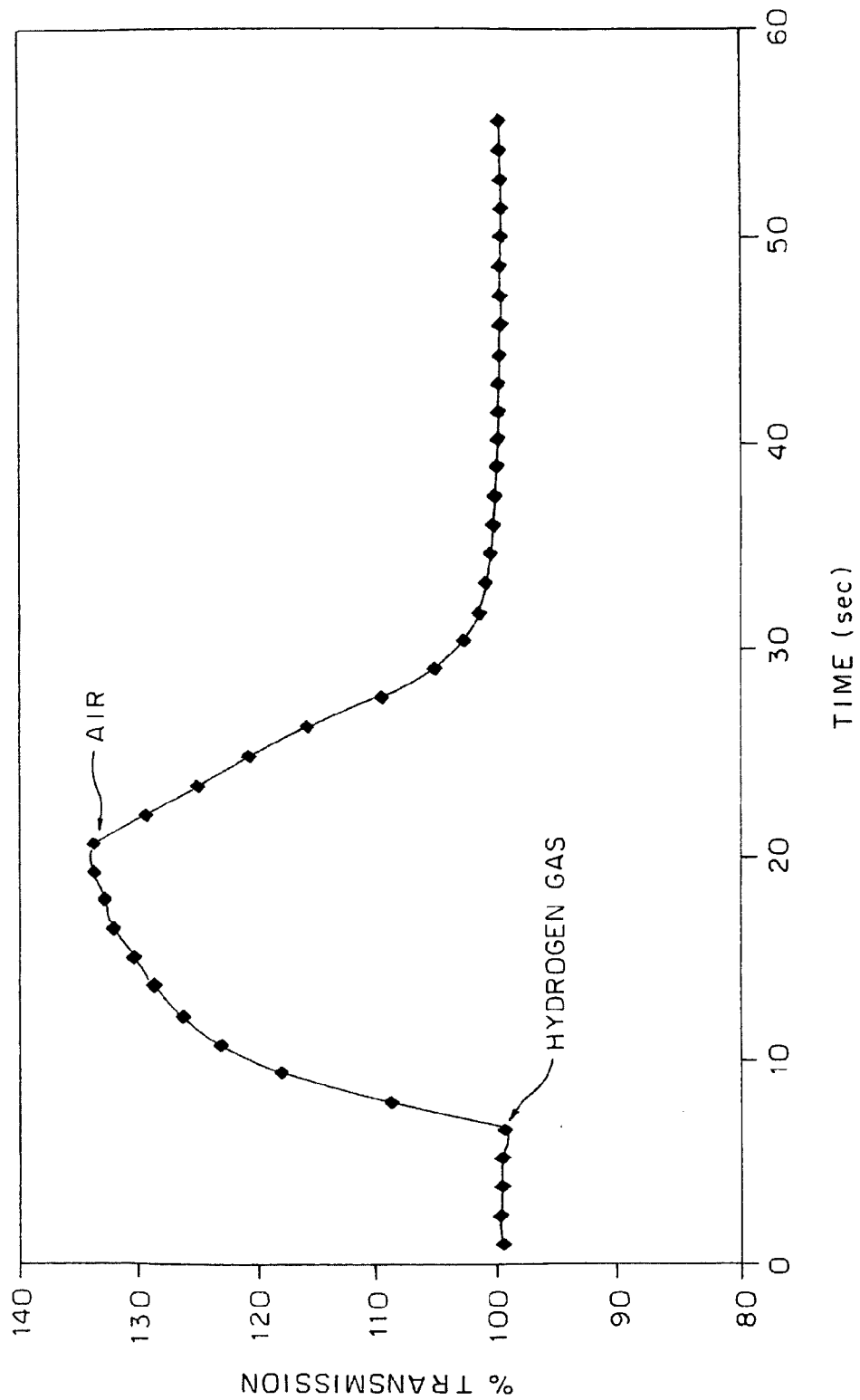
FIG. 2 is a graph showing percent relative transmission versus time for a 20 nm $VO_x$/30 nmPd sensor in the presence of 4% hydrogen.

FIG. 2 is a graph depicting percent relative transmission versus time for a 20 nm VO/30 nrn Pd hydrogen sensor when exposed to a 4% hydrogen environment, and subsequently exposed to air.

The cycling stability of a 20 nm VO/30 nrn Pd hydrogen sensor at 4% hydrogen is shown in the graph of transmission relative percent versus cycle number in FIG. 3, where excellent cycling stability is exhibited during repeated coloring/bleaching cycles. The difference of transmittance between bleached and colored curves does not decrease with cycling.

From the foregoing, it is apparent that ion insertion host capability of the vanadium oxide layer is necessary to obtain stable cycling, and that, in the absence of an ion insertion host (as in the case of $SiO_2$) control experiment stable chemochromic cycling is not obtained due to the fact that palladium hydride is formed and the sensor is destroyed.

The Pd/$V_2O_5$ hydrogen sensor results show that: a proton insertion material is vital to stabilizing the palladium layer, although it does not contribute to the optical response; that the Pd/$V_2O_5$ hydrogen sensor is easy to make via thermal evaporation processes; and that a wide response range of between 1 to 100% $H_2$ concentration is available for detecting hydrogen.

The invention claimed is:

1. An improved method of chemochromic detection of hydrogen gas over a wide range that exhibits stability during repeated coloring/bleaching cycles upon exposure and removal of hydrogen gas, comprising:
   subjecting a sensor structure comprising a substrate, a layer of $V_2O_5$ coated on said substrate, and about a 30 nm layer of palladium (Pd) coated on said layer of $V_2O_5$ to an environment
comprising hydrogen to cause a reaction governed by the equation:

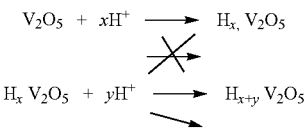

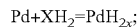

and an optical response governed by the equation:

Pd+$XH_2$=Pd$H_{2x}$;

wherein said $V_2O_5$ layer functions as a $H_2$ insertion host in the Pd/$V_2O_5$ hydrogen sensor, and said Pd layer functions as an optical modulator.

2. The method of detection of claim 1 wherein the Pd/$V_2O_5$ structure is not saturated at 2% $H_2$ or higher.

3. The method of claim 2 wherein hydrogen gas over a wide range that exhibits stability
   during repeated coloring/bleaching cycles is between about 1 to about 100% $H_2$ concentration.

4. The method of claim 1 wherein said palladium layer is deposited by evaporation.

* * * * *